(12) United States Patent
Blalock et al.

(10) Patent No.: US 6,551,348 B1
(45) Date of Patent: Apr. 22, 2003

(54) TEMPERATURE CONTROLLED FLUID THERAPY SYSTEM

(75) Inventors: Allen V. Blalock, Knoxville, TN (US); Mark E. Justice, Powell, TN (US); Benny L. Tanhehco, Powell, TN (US)

(73) Assignee: DeRoyal Industries, Inc., Powell, TN (US)

( * ) Notice: Subject to any disclaimer, the term of this patent is extended or adjusted under 35 U.S.C. 154(b) by 112 days.

(21) Appl. No.: 09/771,025

(22) Filed: Jan. 26, 2001

(51) Int. Cl.$^7$ .................................................. A61F 7/00
(52) U.S. Cl. ......................... 607/104; 165/46; 137/334
(58) Field of Search .............................. 607/104, 108, 607/96, 114; 219/211, 528; 392/470, 472; 126/204; 165/46; 137/334, 341

(56) References Cited

U.S. PATENT DOCUMENTS

| | | | |
|---|---|---|---|
| 2,726,658 A | 12/1955 | Chessey | |
| 3,477,427 A | 11/1969 | Lapidus | |
| 3,918,458 A | 11/1975 | Nethery | |
| 4,112,943 A | 9/1978 | Adams | |
| 4,459,468 A | 7/1984 | Bailey | |
| 4,566,455 A | * 1/1986 | Kramer | 607/109 |
| 4,640,287 A | 2/1987 | Ruderian | |
| 4,821,354 A | 4/1989 | Little | |
| 4,960,103 A | 10/1990 | Urso | |
| 5,097,829 A | 3/1992 | Quisenberry | |
| 5,174,285 A | 12/1992 | Fontenot | |
| 5,183,039 A | 2/1993 | Sarian et al. | |

(List continued on next page.)

FOREIGN PATENT DOCUMENTS

| | | | |
|---|---|---|---|
| EP | 672401 | * | 9/1995 |
| WO | 9857064 | * | 12/1998 |

OTHER PUBLICATIONS

T–300 Motorized Cold Therapy Unit. Author: Unknown. date of publication unknown. The T–300 is a soft bag cold therapy device utilizing a pump to circulate cold water through an applicator. The T–300 used a thermistor as the fluid temperature sensor which was located in the outlet conduit of the bag. The unit also used a thermistor sensor at the fluid return line just prior to the fluid's entry into the fluid reservoir from the applicator to monitor the temperature of the returned fluid to control the fluid flow rate and thus the temperature of the fluid at the applicator. The first date of sale was Dec. 1, 1999.

*Primary Examiner*—John A. Jeffery
(74) *Attorney, Agent, or Firm*—Luedeka, Neely & Graham, P.C.

(57) ABSTRACT

According to the present invention, a temperature controlled therapy device is provided which maintains a desired temperature in a fluid. The temperature controlled therapy device includes a fluid reservoir, a temperature controlled fluid, a watertight blanket having an internal space located therewith, a conduit connected between an exit port of the reservoir and an entry port of the blanket and between an exit port of the blanket and an entry port of the reservoir for defining a fluid circuit within which the temperature controlled fluid may circulate, a pump for circulating the temperature controlled fluid through the fluid circuit, a differential temperature sensor for generating an output signal proportional to a difference in fluid temperature in the blanket and a temperature at a remote location, an absolute temperature sensor for generating an output signal proportional to the temperature at the remote location, a control circuit having as inputs the outputs of the differential temperature sensor and the absolute temperature sensor for generating a control signal for operating the pump in order to maintain a defined temperature range in the fluid in the blanket, and a power supply for supplying power to the device.

21 Claims, 9 Drawing Sheets

U.S. PATENT DOCUMENTS

| | | |
|---|---|---|
| 5,241,958 A | 9/1993 | Noeldner |
| 5,277,695 A | 1/1994 | Johnson, Jr. et al. |
| 5,330,519 A | 7/1994 | Mason et al. |
| 5,371,655 A | 12/1994 | Murdock et al. |
| 5,423,748 A * | 6/1995 | Uhala .......................... 604/67 |
| 5,476,489 A | 12/1995 | Koewler |
| 5,528,485 A | 6/1996 | Devilbiss et al. |
| 5,566,062 A | 10/1996 | Quisenberry et al. |
| 5,647,051 A | 7/1997 | Neer |
| 5,733,319 A * | 3/1998 | Neilson et al. ............. 607/105 |
| 5,865,841 A * | 2/1999 | Kolen et al. ................ 607/104 |
| 5,871,526 A * | 2/1999 | Gibbs et al. ................ 607/104 |
| 5,895,418 A | 4/1999 | Saringer |
| 5,948,012 A * | 9/1999 | Mahaffey et al. ........... 607/104 |
| 6,019,783 A * | 2/2000 | Philips et al. ............... 607/105 |

\* cited by examiner

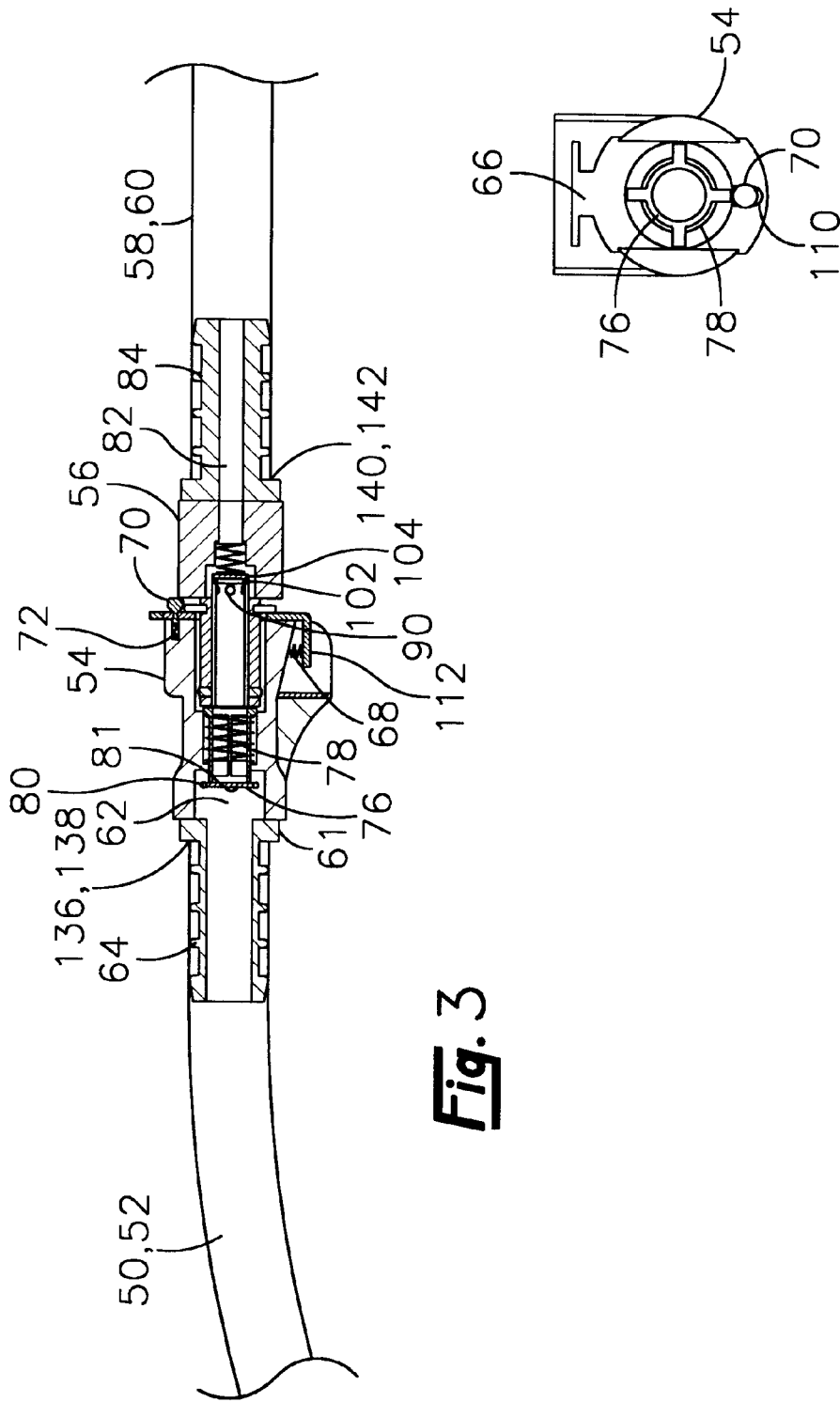

TEMPERATURE CONTROLLED FLUID THERAPY SYSTEM

TECHNICAL FIELD

This invention relates to the field of therapeutic medical devices. More particularly, this invention relates to a temperature controlled fluid therapy system utilizing sensors to provide signals to a continuously variable pump which cycles fluid therapy to an individual.

BACKGROUND OF THE INVENTION

Hot and cold therapies have been used for many years to treat physiological maladies. Ice, one of the more traditional cold therapy methods has the advantage of minimal cost and is easily manufactured. However, traditional ice application methods are not perfect, many patients complaining about leaky ice bags and the inconvenience of refilling the ice bag as the ice melts. Furthermore, traditional ice application methods are not very precise in applying a uniform temperature throughout the injured area. Likewise, the applicator temperature is not easily regulated.

Various mechanical cold and hot therapy systems have been developed to surmount some of the problems associated with the more traditional therapeutic techniques. Continuous flow cold therapy devices utilize a pump to force temperature regulated fluid through a "blanket" or applicator which, in turn, is applied to a patient. However, not all of these mechanical fluid therapy systems give a constant temperature regulation which may be deleterious to patient recovery. Additionally, current temperature sensors are susceptible to the presence of a liquid, resulting in operational fluctuations, unrelated to temperature. These fluctuations make it impossible to control the system temperature precisely.

There is a need for an improved fluid therapy system including improved temperature sensor systems that are inexpensive and not amenable to fluid contamination.

SUMMARY OF THE INVENTION

The foregoing and other needs are met by a temperature controlled therapy device according to the present invention. The temperature controlled therapy device is designed to maintain a desired temperature in a fluid, depending on a user's preference of a hot or a cold therapy treatment. The device includes a fluid reservoir, preferably containing a temperature controlled fluid. The reservoir has an entry and an exit port allowing the fluid to circulate from the reservoir to a watertight blanket. The blanket has an internal space for circulating the fluid therethrough and an entry and an exit port in fluid communication with the reservoir entry and exit ports, respectively. A conduit is connected between the exit port of the reservoir and the entry port of the blanket and between the exit port of the blanket and the entry port of the reservoir. The conduit defines a fluid circuit wherein the temperature controlled fluid circulates from the reservoir to the blanket and from the blanket to the reservoir. The device utilizes a pump to circulate the temperature controlled fluid through the fluid circuit. The device also utilizes a differential temperature sensor to generate an output signal which is proportional to a difference in fluid temperature in the blanket and a temperature at a remote location. An absolute temperature sensor generates an output signal that is proportional to the temperature at the remote location. The outputs from the differential temperature sensor and the absolute temperature sensor are input to a control circuit. The control circuit uses these inputs to generate a control signal which controls the operation of the pump and thereby maintains a defined temperature range within the fluid in the blanket. A power supply supplies power to the device.

BRIEF DESCRIPTION OF THE DRAWINGS

Further advantages of the invention will become apparent by reference to the detailed description when considered in conjunction with the figures, not drawn to scale, wherein like reference numbers indicate like elements through the several views, and wherein:

FIG. 3 is another cross-sectional side view of components of the temperature controlled fluid therapy device in accordance with the invention;

FIG. 4 is a perspective view of a component of the temperature controlled fluid therapy device of FIGS. 2 and 3;

DETAILED DESCRIPTION OF THE INVENTION

Figure 1:
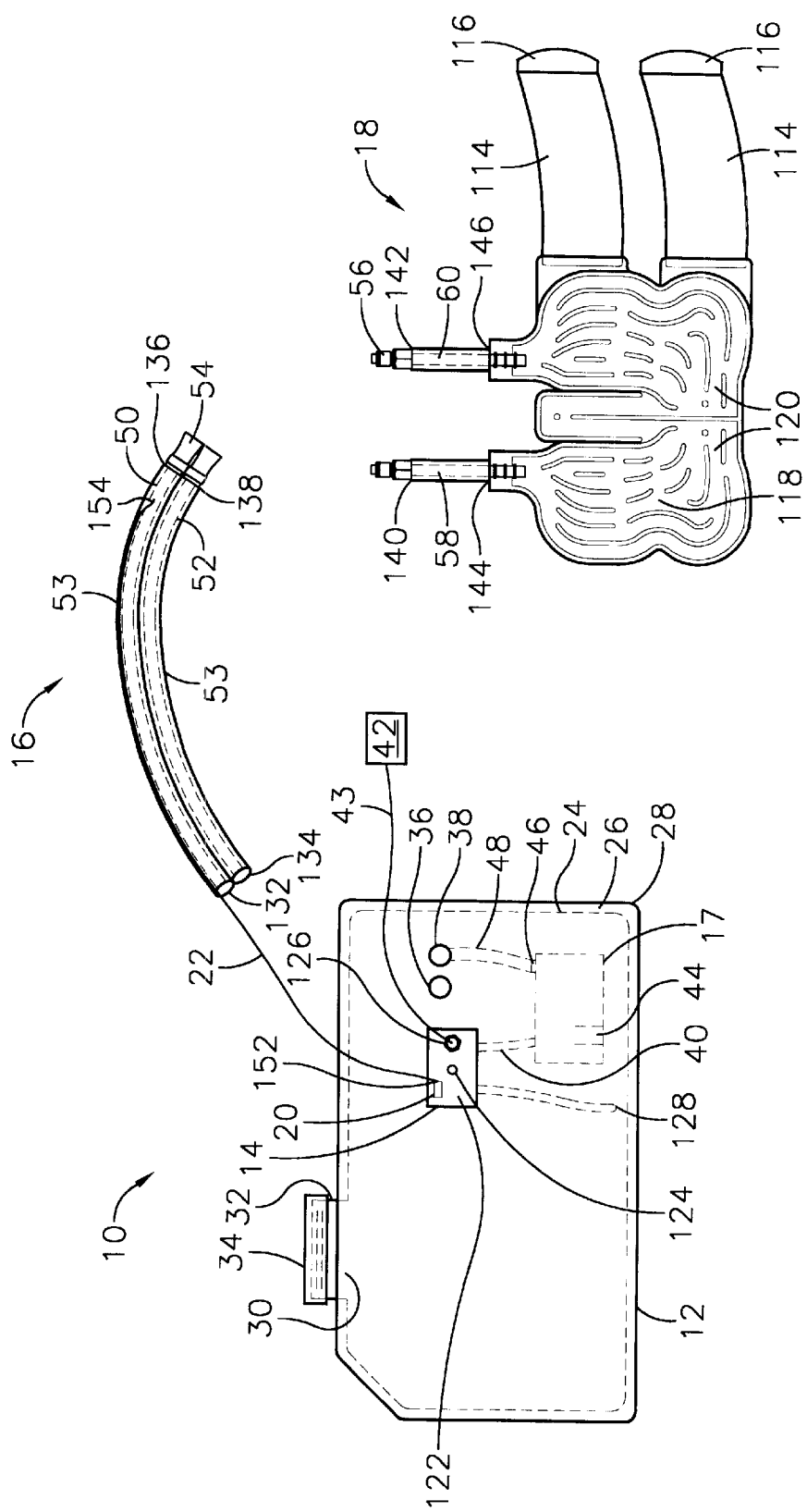
FIG. 1 is a front perspective view of a temperature controlled fluid therapy device in accordance with the invention.

With initial reference to FIG. 1 the invention relates to a temperature controlled fluid therapy device 10 for providing hot and cold therapies to an ailing area of a patient for rehabilitation of the patient. In a preferred embodiment of the invention, the temperature controlled fluid therapy device 10 includes a fluid reservoir 12, a circuit board 14 including a control circuit 129 (FIGS. 5 and 6), a fluid conduit 16, a submersible continuously variable pump 17, a temperature controlled fluid blanket 18 and sensors 20 and 22.

Fluid reservoir 12 is preferably constructed of a thermoplastic material, plastic or rubber, and has a fluid handling capacity of between about 4 liters and about 6 liters. Preferably, fluid reservoir 12 includes an interior wall 24 which forms a cavity 26 between the interior wall 24 and outer wall 28. It is preferred that the cavity 26 be filled with an insulating material such as a gas under vacuum conditions, or styrofoam, Alternatively, the interior wall may be constructed of an insulating material such as foam or plastic, formed adjacent to the outer wall 28. Fluid reservoir 12 includes a fill port 30 which is generally circular in shape having a diameter of between about 3.75 inches and about 4.75 inches. The filler port 30 includes a threaded neck 32 extending outward from the outer wall 28 of the fluid reservoir 12 for threadably engaging a complimentary threaded enclosure 34. It is preferred that the enclosure 34 be constructed so as to insulate the fluid reservoir 12, substantially preventing the evaporation of fluid contained therein. As will be discussed in more detail below, the fluid reservoir 12 preferably includes an entry port 36 and an exit port 38 for admitting and expelling fluid into and out of fluid reservoir 12, respectively.

Figure 8:
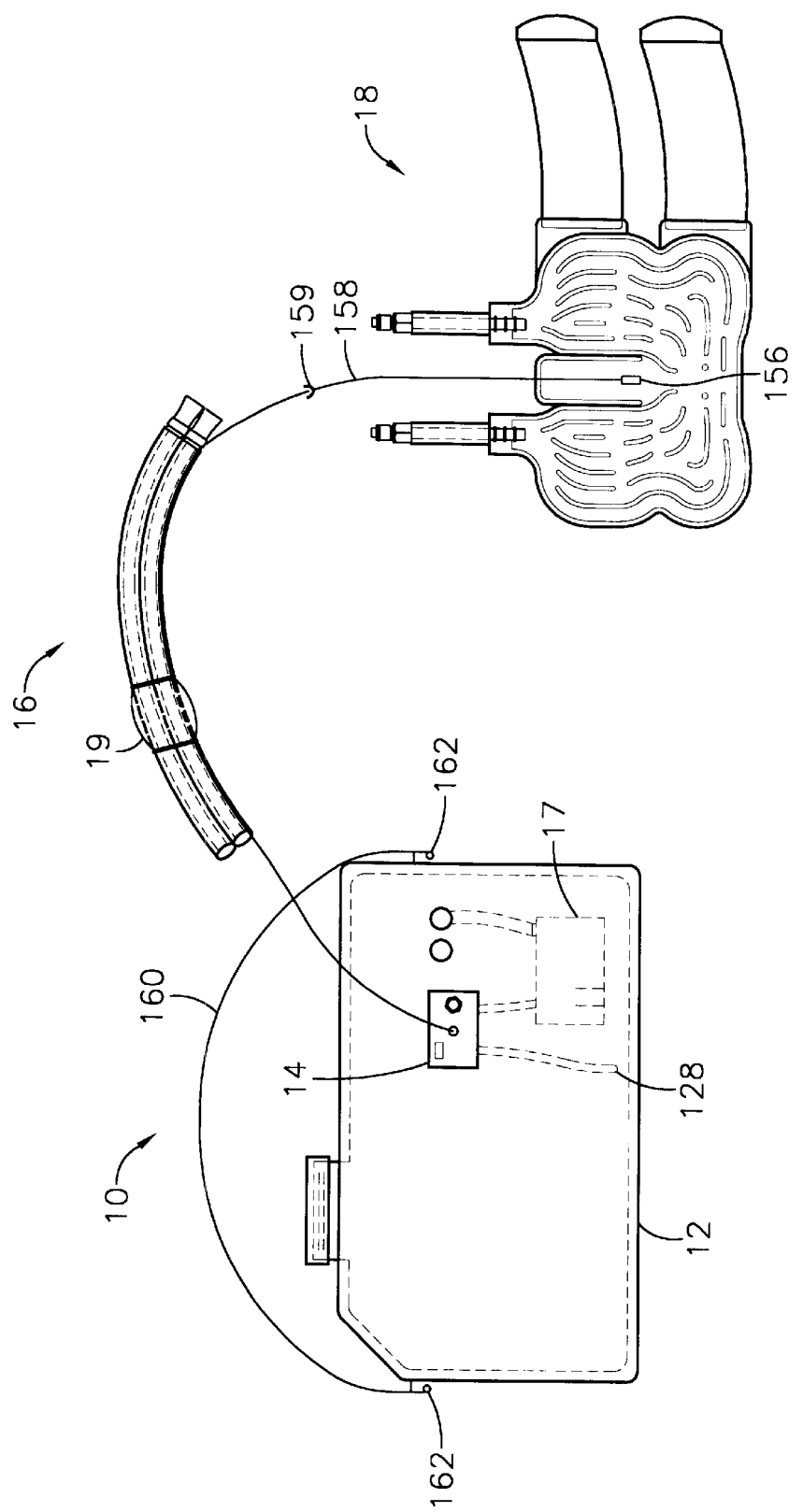
FIG. 8 is a front perspective view of an alternative embodiment of a temperature controlled fluid therapy device in accordance with the invention.

A submersible continuously variable pump 17 is housed within the fluid reservoir 12. The pump 17 preferably has a throughput of between about ¼ gallons/hour and about 10 gallons/hour. The pump 17 is connected to the printed circuit board 14 via wires 40 providing a continuously variable power supply to the pump 17 by utilizing power source 42, to be described more fully below. The submersible pump 17 includes an intake 44 port and an output port 46. When the pump 17 is operating, fluid within reservoir 12 is drawn into the intake port 44 of pump 17 and forced out through the output port 46 of pump 17 and into the connector 48. In an alternative embodiment of the invention, a hand pump 19 (FIG. 8) may also be included, operable to provide an alternative pump means for the device 10. The hand pump 19 is preferably disposed adjacent the fluid conduit 16, and includes two one-way check valves for pumping fluid through the fluid circuit. If a pump 17 is not included in device 10, or if the pump 17 is inoperable or malfunctioning, the hand pump 19 is effective to pump fluid between the reservoir 12 and the watertight blanket 18. The connector 48 is preferably a flexible plastic or rubber hose having a diameter of between about ¼ inches and about ⅜ inches. As shown in FIG. 1, the connector 48 fluidly connects the output port 46 of the pump 17 with the exit port 38 of the fluid reservoir 12. A strap 160 may also be attached via fasteners 162 to the reservoir 12 for ready portability of the fluid therapy device 10 (FIG. 8)

Figure 7:
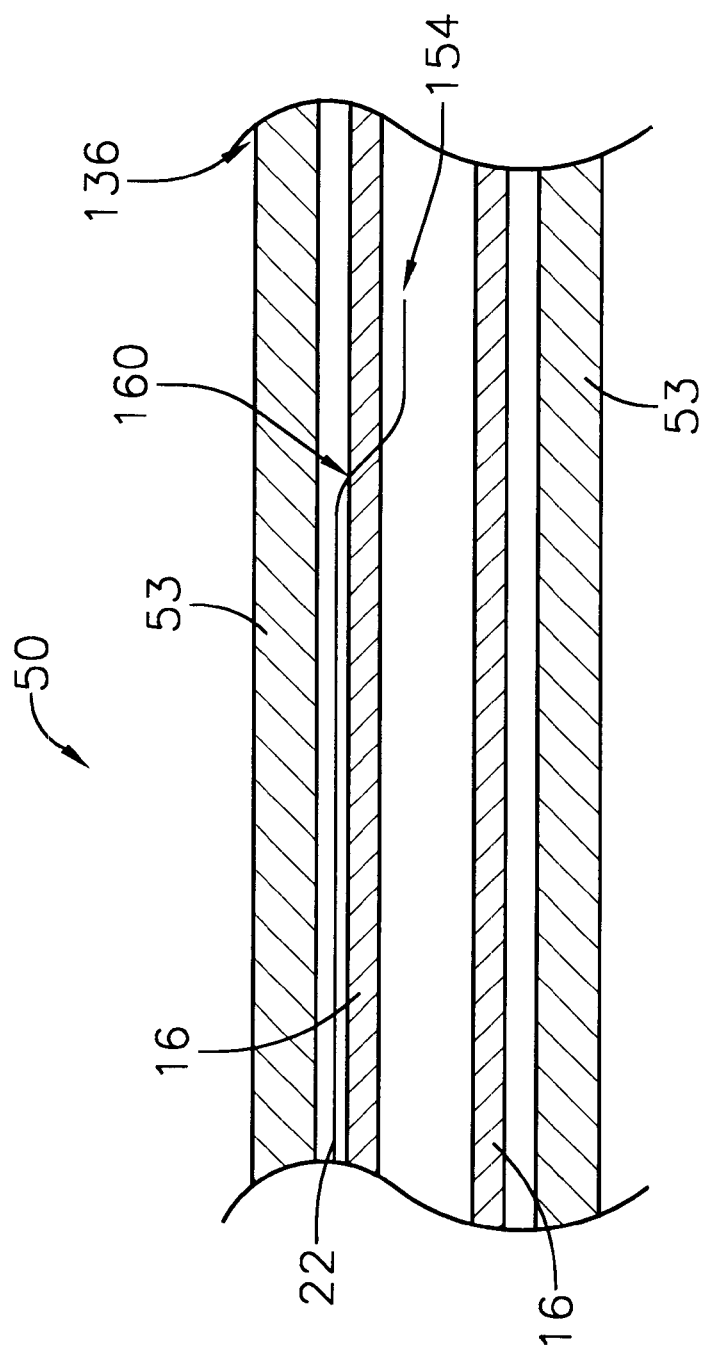
FIG. 7 is another cross-sectional side view of components of the temperature controlled fluid therapy device in accordance with the invention.

The fluid conduit 16 preferably comprises two elongate tubes, intake conduit 50 and output conduit 52, each having first ends 132 and 134, and second ends 136 and 138, respectively. It is preferred that the intake conduit 50 and the output conduit 52 are enclosed with an insulating layer 53 of material such as foam rubber or foam plastic (FIG. 7). The insulating layer 53 of material tends to keep the fluid circulating within the intake and output conduits 50 and 52, respectively, at a relatively constant temperature with little heat transfer into or out of the insulating layer 53. Preferably the elongate tubes, intake conduit 50 and output conduit 52 are composed of similar material as the connector 48, having diameters of between about 0.25 inches and about 0.75 inches and lengths of between about 4 feet and about 8 feet.

Figure 2:
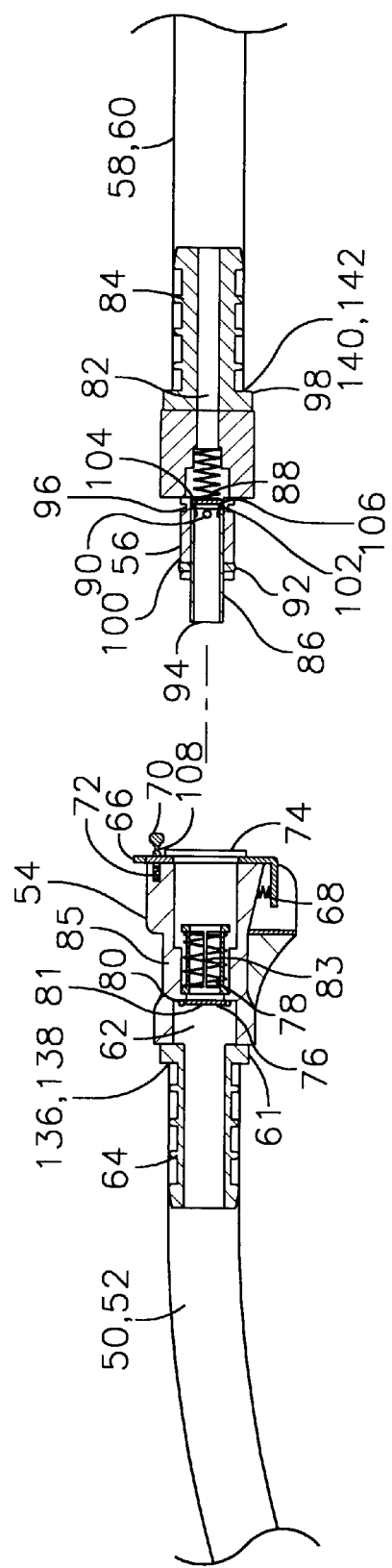
FIG. 2 is a cross-sectional side view of components of the temperature controlled fluid therapy device in accordance with the invention.

The first ends 132 and 134 of elongate tubes 50 and 52 are preferably fixedly secured within the fluid reservoir 12. The first end 132 of the intake conduit 50 is secured within reservoir 12 so that the end 132 is in fluid communication with the interior of the fluid reservoir 12. The first end 134 of the output conduit 52 is preferably secured to the connector 48, forming a fluid path between the output port 46 of the pump 17 and the output conduit 52. As shown in FIGS. 2 and 3, identical female spring actuated quick-release snap fit couplers 54 are attached to the second ends 136 and 138 of the intake conduit 50 and output conduit 52, respectively, and are formed to accept complimentary male snap fit couplers 56 located adjacent to the first ends 140 and 142 of an inflow conduit 58 and outflow conduit 60, respectively, being in fluid communication with the temperature controlled fluid blanket 18. In a preferred embodiment of the invention, the second ends 144 and 146 of the inflow conduit 58 and outflow conduit 60 are fixedly attached to the blanket 18. Preferably, the inflow and outflow conduits 58 and 60 have a length of between about 4 inches and about 8 inches, and a diameter of between about 0.25 inches and about 0.75 inches. It is also preferred that the inflow and outflow conduits 58 and 60 are enclosed by a similar layer of insulating material as described above for the intake and output conduits 50 and 52.

The components of the female and male couplers 54 and 56 operate together to provide fluid communication between the intake and output conduits 50 and 52 and inflow and outflow conduits 58 and 60, respectively, providing a fluid circuit between the reservoir 12 and the blanket 18. As shown in FIGS. 2 and 4, the female coupler 54 includes a flange 61, throat 62, stem 64, locking member 66, locking member spring 68, pin actuator 70, pin actuator spring 72, receiving end 74, throat actuator 76, throat actuator spring 78, o-ring 80, rear wall 81, apertures 83, and body 85. The male coupler 56 includes a throat 82, stem 84, throat actuator 86, throat actuator spring 88, throat actuator orifices 90, o-ring 92, bore 94, recess 96, flange 98, body 100, actuator o-ring 102, and rear wall 104.

The stem 64 of each female coupler 54 is inserted into the second ends 136 and 138 of the intake conduit 50 and output conduit 52. The female coupler 54 is fully seated when the flange 61 lies substantially adjacent to the second ends 136 and 138 of the intake conduit 50 and output conduit 52, respectively. Likewise, the stem 84 of each male coupler 56 is inserted into the first ends 140 and 142 of the inflow conduit 58 and outflow conduit 60. The male couplers 56 are fully seated when the flange 98 lies substantially adjacent to the first ends 140 and 142 of the inflow conduit 58 and outflow conduit 60, respectively. As shown in FIG. 2, when the male and female couplers 54 and 56 are uncoupled, the throat actuators 76 and 86 are not actuated, meaning that the throats 62 and 82 of the female and male couplers 54 and 56 are blocked by the throat actuators 76 and 86. As will be described below, coupling the female coupler 54 with the male coupler 56 actuates both throat actuators 76 and 86, providing fluid communication between the intake conduit 50 and output conduit 52 and the inflow conduit 58 and outflow conduit 60.

As shown in FIG. 2, when the male coupler 56 is uncoupled from the female actuator 54, the spring 88 urges the throat actuator 86 away from the throat 82 so that the throat actuator orifices 90 of the male throat actuator 86 are occluded by the body 100 and the actuator o-ring 102 secured to a rear wall 104 of throat actuator 86 ensures that no fluid may be transported between the inflow and outflow conduits 58 and 60 and the bore 94 of the male throat actuator 86. Similarly, when the female coupler 54 is uncoupled, the spring 78 urges the female throat actuator 76 away from the throat 62 so that the receiving end 74 is occluded by the rear wall 81 and o-ring 80 of the female throat actuator 76 and the apertures 83 are occluded by the body 85 of the female coupler 54, thereby preventing fluid from being transported between the intake and output conduits 50 and 52 and the female coupler 54.

The intake conduit 50 and output conduit 52 and the inflow conduit 58 and outflow conduit 60 are coupled together by releasably connecting each male coupler 56 of the inflow conduit 58 and outflow conduit 60 into each female coupler 54 of the intake conduit 50 and output conduit 52. As best shown in FIG. 3, when the male coupler 56 is inserted into the receiving end 74 of the female coupler 54, the throat actuator 86 and body 100 of the male coupler 56 impinges on the throat actuator 76 of the female coupler 54, thereby compressing throat actuation springs 78 and 88, allowing the female throat actuators 76 to actuate towards the second ends 136 and 138 of the intake conduit 50 and output conduit 52 and the male throat actuator 86 to actuate towards the first ends 140 and 142 of the inflow conduit 58 and outflow conduit 60. As the body 100 of each male coupler 56 impinges on the female throat actuator 76, the female actuators 76 are urged towards the second ends 136 and 138, the rear wall 81 and o-ring 80 gravitating away from the receiving end 74 and into the wider portion of the throat 62. Additionally, the apertures 83 located on the throat actuator 76 also move into the wider throat 62 creating a fluid pathway between the receiving end 74 and throat 62 of the female coupler 54. As the male throat actuator 86 impinges on the female throat actuator 76, the actuator spring 88 compresses and the rear wall 104 and associated actuator o-ring 102 are urged away from the recess 96 allowing the throat actuator orifices 90 to enter into the throat 82 of the male coupler 56, thereby creating a fluid pathway between the bore 94 of the male throat actuator 86 and the throat 82 of the male coupler 56.

As the body 100 of the male coupler 56 enters the receiving end 74 of the female coupler, the o-ring 92 seals against the body 85 of the female coupler 84, preventing leakage between the coupled male and female couplers 56 and 54, respectively. As the male coupler 56 is inserted into the female coupler 54, the body 100 of the male coupler 56 continues to impel the female throat actuator 76 as the facing surface 106 of the male coupler 56 moves the pin actuator 70 against the force of the pin actuator spring 72 until the notch 108 of the pin actuator 70 is aligned with the slot 110 of the locking member 66. Once the notch 108 of the pin actuator 70 is aligned with slot 110, the locking member spring 68 expands, releasing locking member 66 from its unlocked position to releasably engage the recess 96 of the male coupler 56, securing the male coupler 56 to the female coupler 54, thereby providing fluid communication between the fluid reservoir 12 and blanket 18. The male coupler and female coupler 56 and 54 are disengaged by depressing the actuating surface 112 of the locking member 66 which compresses the locking member spring 68, allowing a wide portion of the slot 110 to move towards the pin actuator 70. The wide portion of the slot 110 is wider than the notch 108 diameter of the actuator pin 70 (FIG. 4). As the pin actuator spring 72 expands, the actuator pin 70 is impelled outward so that a wider portion of the actuator pin 70 engages the wider portion of the slot 110 maintaining the locking member 66 away from the recess 96 of the male coupler, so that the female and male couplers 54 and 56 may now be disengaged.

As shown in FIG. 1, the blanket 18 is preferably secured to the second ends 144 and 146 of the inflow and outflow conduits 58 and 60, respectively. However, alternatively, it may be preferred to utilize a releasable coupler between the inflow and outflow conduits 58 and 60 and the blanket 18. The shape of the blanket 18 can be designed to accommodate a variety of rehabilitation area configurations. For example, a different shape can be used to treat a head rehabilitation area compared to the shape used to treat a shoulder or knee rehabilitation area. A plurality of elastic straps 114, including fastening means 116 are used to releasably maintain the blanket 18 adjacent to the area to be rehabilitated. The fastening means 116 are preferably velcro, but male and female snap members are also available. Furthermore, according to the present invention, the releasable snap-fit male and female couplers 56 and 54 allow for quick interchangeability of a specific blanket 18 directed to rehabilitating specific areas of a patient. The blanket 18 includes an interior space 118 for circulating hot or cold fluid pumped from the reservoir 12 by the submersible continuously variable pump 17 through the fluid circuit defined by the output conduit 52, inflow conduit 58, outflow conduit 60, intake conduit 50, pump 17, reservoir 12 and blanket 18. It is preferred that the interior space 118 of the blanket 18 forms a plurality of channels 120 for cycling the fluid through the blanket at a rate of between about ¼ gallons/hour and about 10 gallons/hour. Blanket 18 is preferably formed of plastic, rubber, and non-woven material.

As shown in FIG. 1, the printed circuit board 14 is attached to outer wall 28 of the fluid reservoir 12. Preferably, the circuit board 14 is enclosed by a faceplate 122, including a reservoir 12 fill indicator means 124, and a power source connection port 126. The power source connection port 126 is configured for connecting an alternating current (AC) to direct current (DC) adapter to an AC power source 42 or, alternatively, a DC power source 42 may be directly connected to the power source connection port 126 via electrical connector 43.

Figure 9:
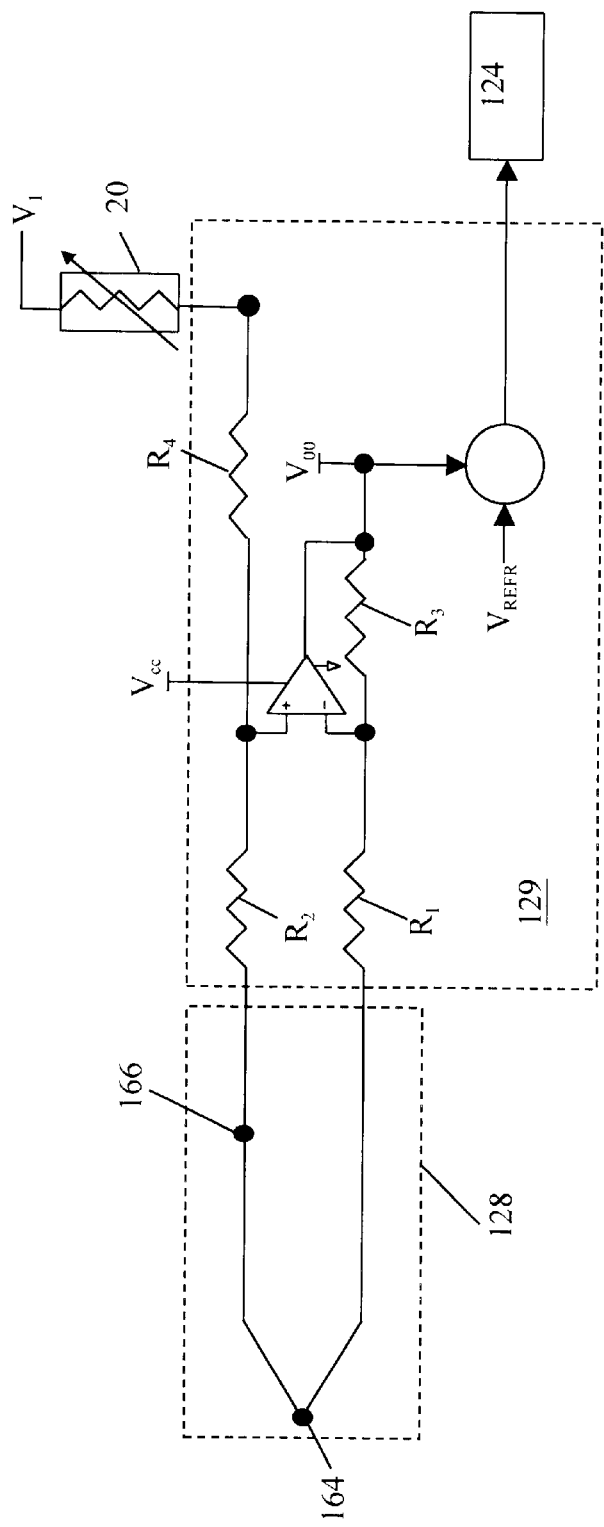
FIG. 9 is a circuit diagram illustrating the reservoir fluid sensor and associated output voltage input into the fill indicator means; and, FIG. 10 is a circuit diagram illustrating the reservoir fluid sensor and associated output voltage input into the fill indicator means and the temperature sensors and associated output voltage input into the pulse width modulator.

The fill indicator means 124 indicates a fluid fill condition to an operator or user. The fill indicator means 124 may be a dual-mode light, a green signal indicating a no-fill condition and a red signal indicating a fluid fill alert. Preferably, the fill indicator means is electrically connected to the control circuit 129 and also to a reservoir sensor 128 located in the interior space of the reservoir 12 (FIG. 9). The sensor 128 may be capable of sensing a plurality of fluid conditions within reservoir 12, such as the fluid temperature and quantity. In one embodiment, the sensor 128 is a thermistor which is operable to provide a voltage signal to the control circuit 129 proportional to the temperature of the fluid within the reservoir 12.

For a cold therapy application the voltage signal $V_{oo}$ provided by the sensor 128 is compared to a voltage $V_{REFR}$ corresponding to the preferred optimal fluid temperature of between about 35° F. and about 55° F. within the fluid reservoir 12. If the sensed temperature is about 55° F. or less, the fill indicator means 124 will indicate a no-fill condition. However, if the sensed temperature is greater than about 55° F., the fill indicator means 124 will indicate a fill condition, alerting a user or operator to add more ice or cold fluid to the reservoir 12.

For a hot therapy application the voltage signal $V_o$ provided by the sensor 128 is compared to a voltage $V_{REFR}$ corresponding to the preferred optimal fluid temperature of between about 95° F. and about 110° F. within the fluid reservoir 12. If the sensed temperature is between about 95° F. to about 110° F., the fill indicator means will indicate a no-fill condition. However, if the sensed temperature is less than 95° F., the fill indicator means will indicate a fill condition, alerting a user or operator to add more hot fluid to the reservoir 12. For a device 10, having an internal refrigeration or heating means within the reservoir 12, the signal provided by the sensor 128 operates as a control signal, enabling or disabling the refrigeration or heating means. Table 1 lists preferred values for the components of FIG. 9.

TABLE 1

| | |
|---|---|
| $V_1$ | ~5.0 V |
| $V_2$ | ~2.5 V |
| $V_{REFR}$ | ~3.38 V |
| $R_1$ | ~100 ohms |
| $R_2$ | ~100 ohms |
| $R_3$ | ~69.8 kohms |
| $R_4$ | ~69.8 kohms |
| $R_5$ | ~1.74 kohms |

In an alternative embodiment of the invention, a thermocouple may be used in place of the thermistor as the sensor 128 which is also operable to provide a temperature of the fluid within the reservoir 12. As described below, the output voltage signal from the thermocouple sensor is proportional to the temperature difference between two wire junctions, 164 and 166. Since the output voltage signal of the thermocouple sensor is proportional to the temperature difference between the two junctions 164 and 166, the thermocouple sensor cannot provide an absolute temperature indication at the junctions. Therefore, by utilizing a cold junction compensation circuit such as thermistor 20, the signal provided by the thermistor sensor 20 located adjacent to the circuit board 14 changes with and compensates for the changes in the ambient temperature to determine an absolute temperature and output voltage $V_{OO}$ at junction 164 of the thermocouple (FIG. 9). Since the thermocouple is inherently insensitive to water permeation, the thermocouple sensor is operable to provide a reservoir temperature indication signal and/or control signal $V_{OO}$ which is used as described above without erroneous indications due to fluid permeation.

Furthermore, an audible signaling device may be used to indicate a fluid fill alert, audibly signaling a fluid fill condition to an operator or user. Similarly, a fluid level indicator and temperature indicator may be used to alert the operator to the fluid conditions within the reservoir 12.

Preferably, the circuit board 14 is disposed between the outer wall 28 and interior wall 24 of the fluid reservoir 12 so that the fluid within reservoir 12 does not come into contact with the circuit board 14. That is, it is preferred that the circuit board 14 is maintained in a dry state, ensuring the operability of the electrical connections of the board 14. The wires 40 connecting the circuit board to the pump 17 pass through an aperture formed in the interior wall 24 of the reservoir 12, and a sealant or gasket is used around the wires 40 at the point where they pass through the aperture for preventing fluid from entering the space between the interior wall 24 and exterior wall 28, where the circuit board 14 is located.

According to a preferred embodiment of the invention, two sensors 20 and 22 are utilized to determine a control signal, which controls the operation of the submersible pump 17. Preferably, when a DC or AC power source 42 is connected to the power source connector port 126 a voltage is always applied to the submersible pump 17 via the conducting wires 40. The power provided to the submersible pump 17 is based on the control signal determined from the output of sensors 20 and 22. Preferably, sensor 20 is a thermistor type sensor having a variable resistance of between about 1,000 ohms and 10,000 ohms. The resistance of a thermistor type sensor varies exponentially according to the surrounding temperature and is operable to output an absolute temperature reading. As shown in FIG. 1, the thermistor sensor 20 is adjacently located to the circuit board 14, and similarly protected between the interior wall 24 and exterior wall 28 as the circuit board 14 from potential fluid permeation. It is preferable to maintain the thermistor sensor 20 in a "dry" state since fluid permeation impinging on the thermistor sensor 20 may tend to cause the thermistor sensor 20 to provide an erroneous absolute temperature signal.

For a cold fluid therapy device, it is preferable to maintain the fluid within a desired temperature range so that maximal beneficial results are seen at the treatment area of a user or patient. According to the invention, to obtain an accurate blanket 18 temperature reading, it is preferable to sense the temperature of the fluid circulating through the blanket 18 as close as possible to the blanket 18. Preferably, the fluid temperature is sensed at a location adjacent to the second end 136 of the intake conduit 50 which when connected to the outflow conduit 60 tends to give a close approximation of the temperature of the fluid circulating through the blanket 18.

Therefore, it is preferred to use a sensor which tends to be impervious to fluid permeation, such as a thermocouple sensor 22. The thermocouple sensor 22 is preferably a T-type thermocouple (constantan member 148 and copper member 150 (FIG. 6)), but a K-type thermocouple consisting of a chromell member and alumel member, or other types of temperature sensors, are also viable sensors. Accordingly, the thermocouple sensor 22 includes a cold junction 152 and a hot junction 154, and the output signal from the thermocouple sensor 22 is proportional to the temperature difference between the cold and hot junctions 152 and 154, respectively. Since the output signal of the thermocouple sensor 22 is proportional to the temperature difference between the cold and hot junctions 152 and 154, the thermocouple sensor 22 cannot provide an absolute temperature indication at junctions 152 or 154. By utilizing the absolute (compensating) temperature signal provided by the thermistor sensor 20, it is possible to determine the absolute temperature at junction 154 of the thermocouple sensor 22.

According to a preferred embodiment of the invention, the cold junction 152 of the thermocouple sensor 22 is adjacently located to the thermistor sensor 20 on the circuit board 14. An approximate temperature of the cold junction 152 of the thermocouple sensor 22 may be determined by locating the cold junction 152 of the thermocouple sensor 22 adjacent to the thermistor sensor 20 since the thermistor sensor 20 is providing an absolute temperature signal. As described above, the thermocouple sensor 22 provides a signal proportional to the temperature difference between the cold and hot junctions 152 and 154. Therefore, by utilizing the sensed thermistor sensor 20 signal to determine approximately the cold junction 152 temperature, the hot junction 154 temperature is determined by subtracting the cold junction 152 temperature from the sensed temperature difference of the thermocouple sensor 22, providing a temperature of the hot junction 154.

FIG. 7 depicts a preferred embodiment for the location of the hot junction 154 of the thermocouple sensor 22. As shown, the thermocouple 22 is preferably located between the insulating layer 53 and the fluid conduit 16. The thermocouple 22 extends from the cold junction 152 adjacently located to the circuit board 14 to the hot junction 154, which preferably penetrates through an orifice 160 into the intake conduit 50. Preferably, the aperture 160 and hot junction 154 are located adjacent to the second end 136 of the intake conduit 50. It is preferred that the orifice 160 is sealed around the sensor 22 by using epoxy, or sealant. Accordingly, by locating the hot junction 154 of the thermocouple sensor 22 adjacent to the second end 136 of the intake conduit 50 and thereby adjacent to the first end 142 of the outflow conduit 60 of the blanket 18, an approximate temperature of the fluid within the blanket 18 may be determined due to the proximity of the hot junction 154 with respect to the fluid exiting the blanket 18. Correspondingly, the device 10 provides hot or cold fluid therapies to a user without the concern of erroneous temperature readings due to water permeation of the thermocouple sensor 22, since the thermocouple 22 is substantially insensitive to water permeation.

In another embodiment of the invention, the hot junction 154 of thermocouple sensor 22 does not penetrate the intake conduit 50, but is instead located between the fluid conduit 16 and the insulating layer 53. Accordingly, it is still possible to obtain an accurate approximation of the fluid temperature within the blanket 16, however, there may be a slight delay in sensing the actual fluid temperature due to the material properties of the fluid conduit 16. Therefore, for this latter sensor configuration, a 'warm-up' time may be necessary to achieve an appropriate fluid temperature determination.

Figure 5:
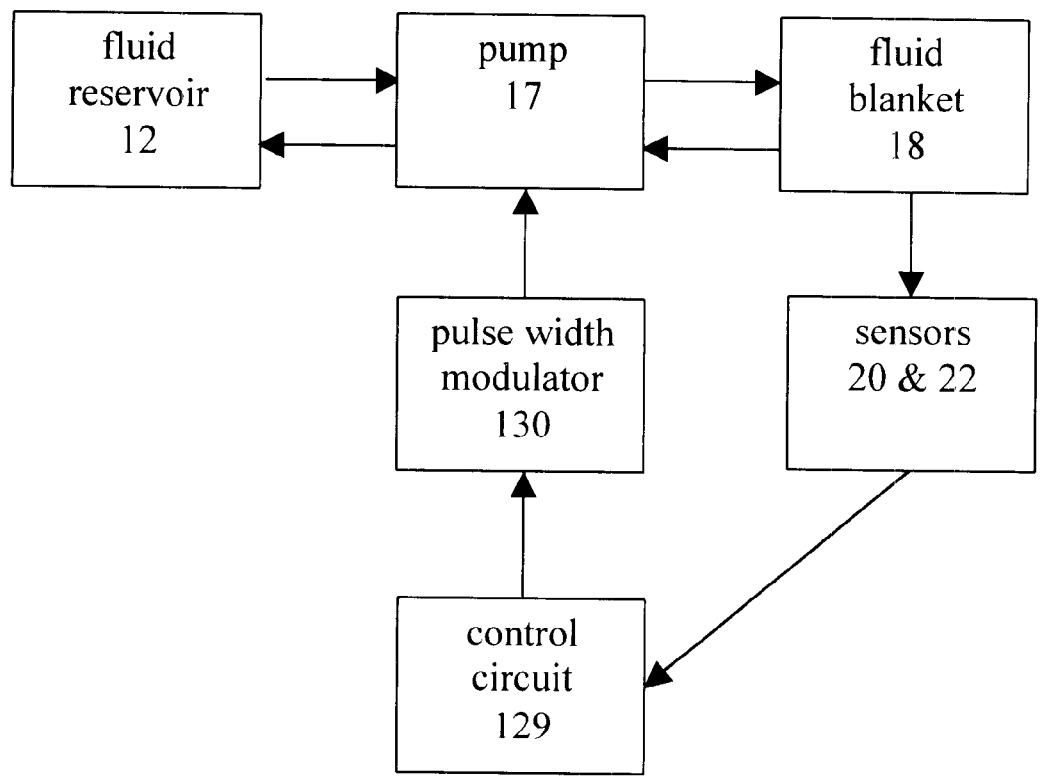
FIG. 5 is a block diagram illustrating the operation of the temperature controlled fluid therapy device.
Figure 6:
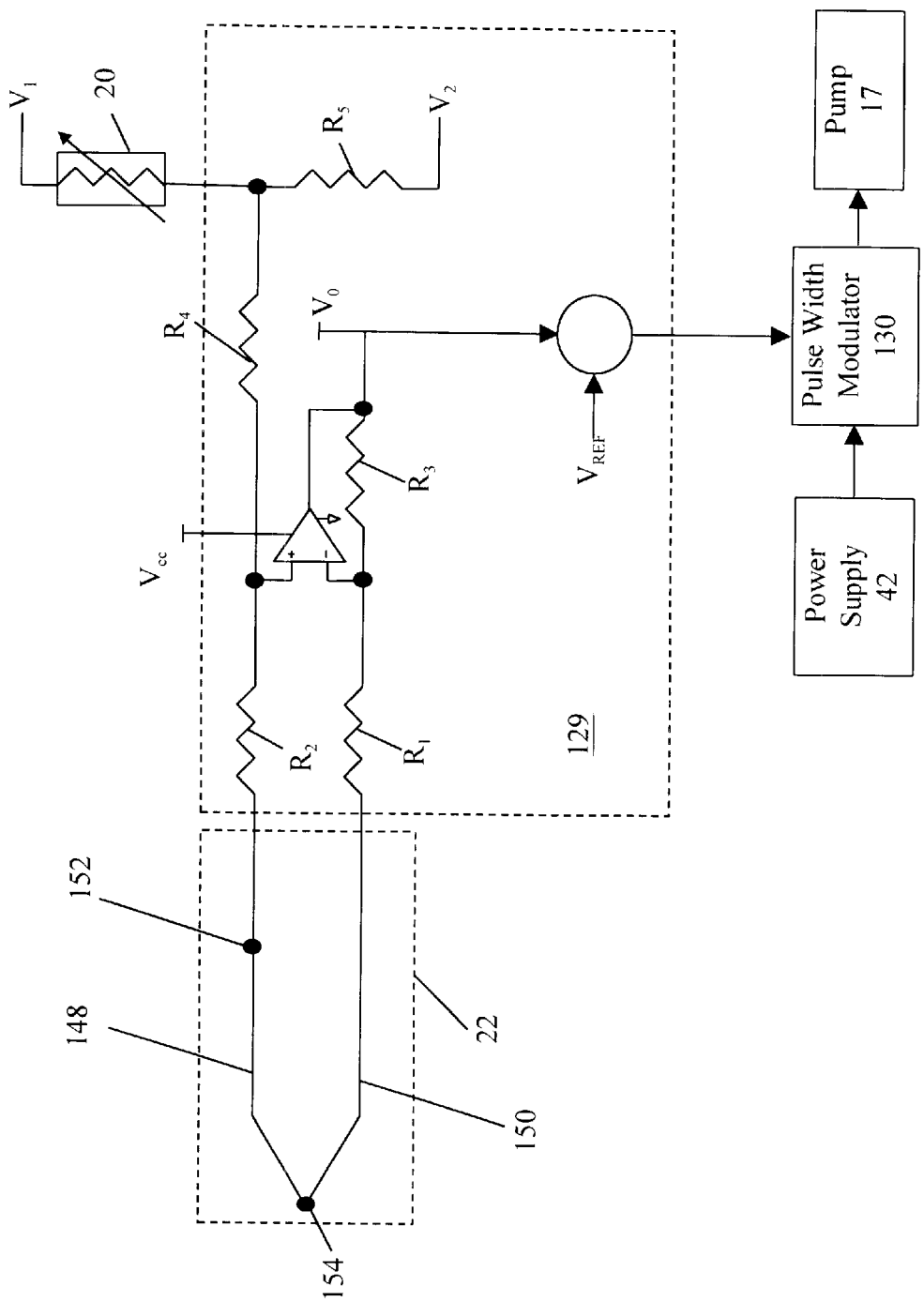
FIG. 6 is a circuit diagram illustrating the temperature sensors and associated output voltage input into the pulse width modulator.

Since the temperature of the fluid flowing throughout the temperature controlled fluid therapy device 10 is in constant flux, the hot junction 154 temperature will vary correspondingly. Therefore, it is possible to regulate the temperature of the fluid within device 10 by using the varying hot junction temperature as an input to a control circuit 129. Referring to FIG. 5, the control circuit 129 utilizes the thermistor sensor 20 and thermocouple sensor 22 signals to generate a control signal which is input to a calibrated pulse width modulator 130. More particularly, and with additional reference to FIG. 6, the control circuit 129 generates an output voltage $V_0$ which varies according to the fluctuating fluid temperature. Table 2 lists preferred values for the circuit components of the control circuit 129 for a cold therapy device 10.

TABLE 2

| | |
|---|---|
| $V_1$ | ~5.0 V |
| $V_2$ | ~2.5 V |
| $V_{REF}$ | ~3.08 V |
| $R_1$ | ~100 ohms |
| $R_2$ | ~100 ohms |
| $R_3$ | ~69.8 kohms |
| $R_4$ | ~69.8 kohms |
| $R_5$ | ~1.74 kohms |

According to the invention, the varying voltage $V_o$ is compared to the reference voltage $V_{REF}$ and the result is used to control the pulsewidth of a pulse output from the voltage controlled pulse width modulator 130. For a cold therapy device the reference voltage $V_{REF}$ corresponds to a set-point temperature of between 35° F. and about 55° F. The voltage $V_o$ is proportional to a function of the cold junction temperature (thermistor signal) plus another function of the temperature difference between the hot and the cold junctions 154 and 152 (thermocouple signal), respectively. Additionally, for a hot fluid therapy application, the control circuit 129 utilizes a set point temperature of the fluid of between about 95° F. and about 110° F., essentially comparing the hot junction 154 temperature with the set point temperature to generate a control signal which is input to the pulse width modulator 130.

Accordingly, the pulse width modulator 130 utilizes the control signal output from the control circuit 129 to modulate the width of a pulse which is used to control the operation of the pump 17. More specifically, the duty cycle of the pulse width modulated signal is continuously varying according to the varying temperature of the fluid at the hot junction 154 of the thermocouple sensor 22. The varying pulse duty cycle output from the calibrated pulse width modulator 130 controls the average power delivered to the submersible pump 17 via power source 42, therefore controlling the speed of the continuously variable submersible pump 17. The pulse width modulator 130 is calibrated to vary the duty cycle of the pulse based on the control signal output from the control circuit 129. For example, when the control circuit 129 determines that the hot junction 154 temperature of the thermocouple is about equal to the set point temperature, the control circuit 129 sends a corresponding control signal to the pulse width modulator 130. In response, the pulse width modulator 130 modulates the pulse width modulated signal such that pump 17 is operating at about the mid-range of between about ¼ gallons/hour and about 10 gallons/hour.

Depending on the application of the temperature controlled fluid therapy device 10, that is, cold or hot fluid therapy applications, the control signal output from the control circuit 129 is controlled accordingly. For a cold fluid therapy application, as the hot junction 154 temperature increases, the control signal output from the control circuit 129 will vary correspondingly and the duty cycle of the pulse output from the pulse width modulator 130 will increase, causing the pump rate to increase which correspondingly increases the flow of cool fluid flowing from within reservoir 12 to the blanket 18. If the temperature at the hot junction 154 decreases below the set point temperature, the duty cycle of the pulse will correspondingly decrease, to a point where the pump 17 is nearly stopped. However, as described above, preferably there is always power applied to the pump 17, the duty cycle of the pulse output from the pulse width modulator varying the supplied power according to the hot junction temperature 154. On the other hand, for a hot fluid therapy application, as the hot junction 154 temperature decreases, the control signal output from the control circuit 129 will vary correspondingly and the duty cycle of the pulse output from the pulse width modulator 130 will increase, causing the pump rate to increase which correspondingly increases the flow of hot fluid flowing from within reservoir 12 to the blanket 18.

In an alternative embodiment of the invention, it is preferable to control the fluid temperature within the blanket 18 based on the skin temperature of the individual using the device 10. Research has determined the point at which neurons in the skin begin reactivating. Therefore, it would be preferable to measure the skin temperature to control the neuron firing. Accordingly, a thermistor sensor 156 is adjacently located to the blanket 18 (FIG. 8). The thermistor sensor 156 is connected to the circuit board 14 via electrical connector 158. The electrical connector 158 is preferable an insulated conductor, such as insulated copper wire, and may be contained between the insulating layer 53 and the conduit 16, or alternatively, the connector 158 may be externally located with respect to the insulating layer 53. The electrical connector 158 preferably includes a coupling 159, which allows the connector 158 to be disconnected when it is desired to disconnect the blanket 18 from the fluid conduit 16. In this embodiment of the invention, the thermocouple sensor 22 is not a necessary component of device 10 for measuring the temperature of the blanket 10. Depending on the particular blanket 18, the thermistor 156 is preferably located directly adjacent to the rehabilitation area, obtaining the most accurate skin temperature when the blanket 18 and fluid are applied to the individual. In this embodiment, since the thermistor 156 is at a location where there is no potential water contamination, an absolute temperature indication of the skin is available without the possibility of erroneous measurements due to fluid permeation of the thermistor 156.

The control circuit 129 compares the thermistor 156 signal to a reference voltage $V_{REF}$, inputting the result to the pulse width modulator 130. The pulse width modulator 130 varies the duty cycle of the pulses according to the result, controlling the operation of the pump 17, as discussed previously.

According to the invention, since the pump 17 speed varies based on the duty cycle of the pulse output from the pulse width modulator 130, the frequency of the pulses is not a controlling factor. However, the armature of the pump 17 tends to vibrate at the frequency of the pulse width modulated signal, and signal frequencies in the audible range (<20 kHz) tend to make for a noisy pump. According to a preferred embodiment of the invention, the frequency of the pulses output from the pulse width modulator 130 is adjusted by modulation above the audible range (>20 kHz), tending to provide a quieter temperature controlled fluid therapy device 10.

Figure 10:
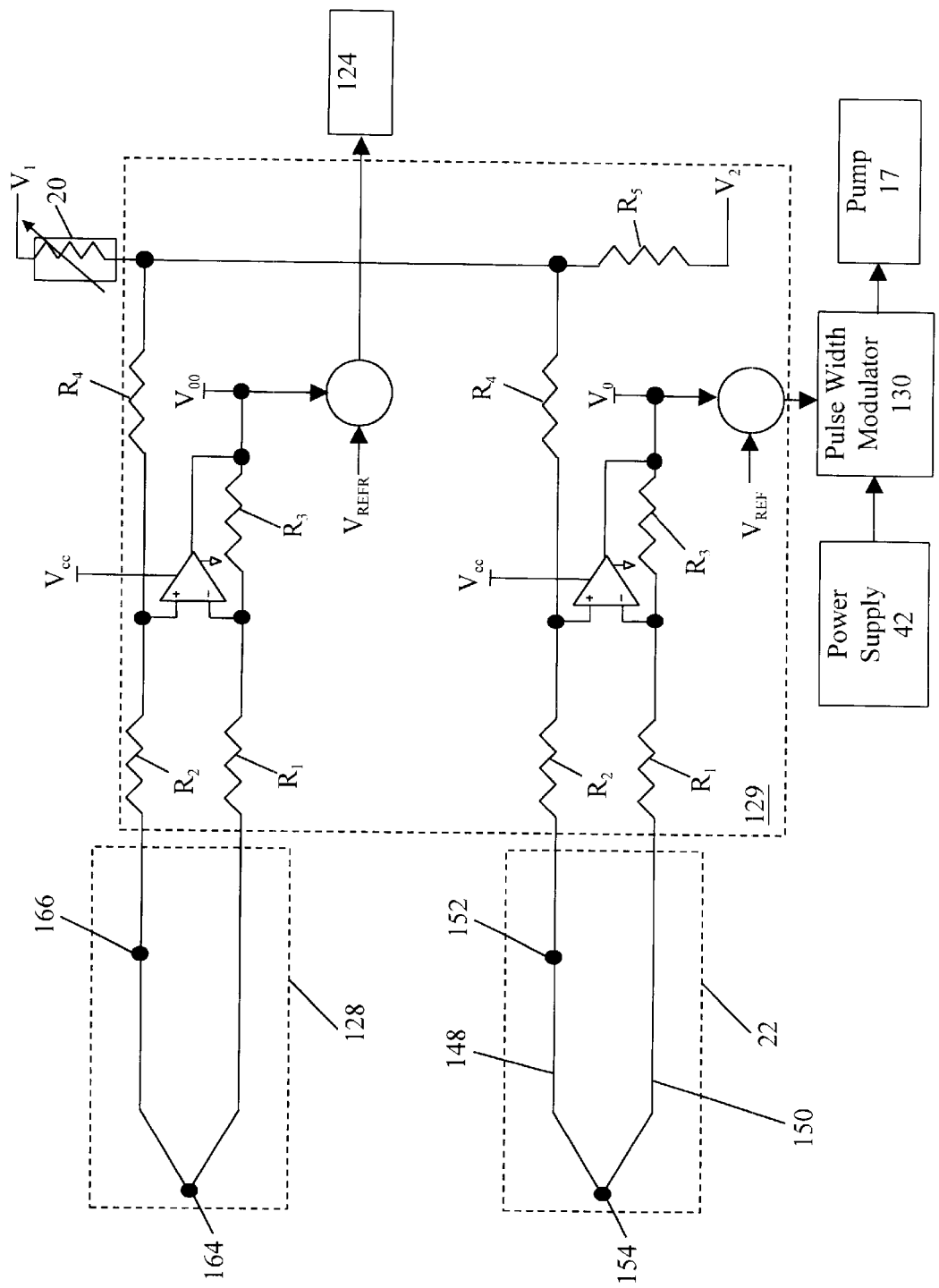

Once the intake conduit 50 and output conduit 52 and the inflow conduit 58 and outflow conduit 60 are connected, a patient may now utilize the temperature controlled fluid therapy device 10 to treat an injured or sore area by applying the blanket 18 thereto. Depending on the application, hot or cold fluid therapy, the fluid reservoir is filled with hot or cold fluid via fill port 30. The user can place the blanket over the treatment area before or after a DC or an AC power source is plugged into the power source connection port 126, immediately providing power to the pump 17. As described above, the control circuit 129 utilizing sensors 20 and 22 automatically regulates the amount of hot or cold fluid flowing to the blanket 18. If the hot or cold fluid within reservoir 18 drops below or above a preferred fluid temperature, the fill indicator means 124 will communicate the condition to the user or operator, who may then add hot or cold fluid to the reservoir 12 (FIG. 10).

It is contemplated, and will be apparent to skilled in the art from the preceding description and the accompanying drawings, that modifications and changes may be made in the embodiments of the invention. For example, the intake and output conduits 50 and 52 and inflow and outflow conduits 58 and 60 can be one continuous piece, that is, not including the male and female couplers 54 and 56. Also, the pump can be externally located from the reservoir 12 controlling the flow of fluid from the reservoir 12 to the blanket 18. Additionally, reservoir 12 can contain refrigeration and/or heating capability and related circuitry for automatically regulating the temperature of the fluid within reservoir 12. Moreover, a fluid fill line and drain line can be attached to a fluid fill port and drain port on reservoir 12 which automatically fills reservoir 12 with hot or cold fluid upon a sensed level/temperature condition of reservoir 12, draining fluid as new fluid is added to reservoir 12. Accordingly, it is expressly intended that the foregoing description and the accompanying drawings are illustrative of preferred embodiments only, not limiting thereto, and that the true spirit and scope of the present invention be determined by reference to the appended claims.

What is claimed is:

1. A method of providing therapeutic care to an individual by controlling a temperature of a temperature controlled therapeutic device, the method comprising the steps of:
   (a) providing a temperature controlled fluid to a reservoir having an entry port and an exit port, the reservoir containing a continuously variable speed circulating pump in fluid communication with the entry and exit ports of the reservoir,
   (b) providing a temperature controlled blanket to the treatment area of an individual, the blanket including a fluid entry port and a fluid exit port and an internal space for circulating the temperature controlled fluid therethrough,
   (c) providing a fluid conduit connecting the exit port of the reservoir with the entry port of the temperature controlled blanket and the entry port of the reservoir to the exit port of the fluid controlled blanket, the connected fluid conduit defining a fluid circuit therebetween,
   (d) providing a pulse width modulator for continuous variable speed control of the pump by controlling an average power delivered to the pump,
   (e) determining a temperature of the temperature controlled blanket,
   (f) providing a control signal to the pulse width modulator to vary the average power delivered to the pump, the control signal derived from the temperature of the temperature controlled blanket, and
   (g) adjusting the speed of the pump based on the control signal, thereby controlling the amount of temperature controlled fluid provided to the temperature controlled blanket via the fluid circuit.

2. The method of claim 1, wherein step (e) includes measuring a temperature at a location adjacent to the fluid reservoir using a thermistor sensor.

3. The method of claim 1, wherein step (e) includes measuring a temperature at location adjacent to the temperature controlled blanket utilizing a hot and a cold junction of a thermocouple sensor.

4. The method of claim 1, wherein step (f) includes adjusting a pulsewidth of a pulse width modulated signal based on the temperature of the temperature controlled blanket.

5. A temperature controlled therapy device for maintaining a desired temperature in a fluid comprising:
   a fluid reservoir having entry and exit ports,
   a temperature controlled fluid,
   a watertight blanket having an internal space located therewith and entry and exit ports,
   a conduit connected between the exit port of the reservoir and the entry port of the blanket and between the exit port of the blanket and the entry port of the reservoir for defining a fluid circuit within which the temperature controlled fluid may circulate,
   a continuously variable pump for circulating the temperature controlled fluid through the fluid circuit,
   a pulse width modulator for controlling an average power delivered to the pump,
   an absolute temperature sensor disposed adjacent to the watertight blanket for being located adjacent to a skin area of a user for generating an output signal proportional to a skin temperature of the user that is using the device,
   a control circuit having as an input the output of the absolute temperature sensor for generating a control signal to the pulse width modulator for operating the pump in order to maintain a defined temperature range in the fluid in the blanket, and
   a power supply for supplying power to the device.

6. A temperature controlled therapy device for maintaining a desired temperature in a fluid comprising:
   a fluid reservoir having entry and exit ports,
   a temperature controlled fluid,
   a watertight blanket having an internal space located therewith and entry and exit ports, a conduit connected between the exit port of the reservoir and the entry port of the blanket and between the exit port of the blanket and the entry port of the reservoir for defining a fluid circuit within which the temperature controlled fluid may circulate, a pump for circulating the temperature controlled fluid through the fluid circuit, a differential temperature sensor for generating an output signal proportional to a difference in fluid temperature in the blanket and a temperature at a remote location, an absolute temperature sensor for generating an output signal proportional to the temperature at the remote location, a control circuit having as inputs the outputs of the differential temperature sensor and the absolute temperature sensor for generating a control signal for operating the pump in order to maintain a defined temperature range in the fluid in the blanket, and a power supply for supplying power to the device.

7. The temperature controlled therapy device of claim 6, wherein the differential temperature sensor is a thermocouple having a cold junction and a hot junction, wherein the hot junction is adjacently located to the exit port of the watertight blanket and the cold junction is adjacently located to the control circuit.

8. The temperature controlled therapy device of claim 6, wherein the absolute temperature sensor is a thermistor adjacently located to the control circuit.

9. The temperature controlled therapy device of claim 6, wherein the control signal generated by the control circuit is responsive to the temperature at a hot junction of a thermocouple.

10. The temperature controlled therapy device of claim 6, wherein the pump is a continuously variable speed submersible pump and the device further comprises a pulse width modulator, wherein the control signal generated by the control circuit is utilized by the pulse width modulator to modulate a width of a pulse width modulated signal that controls the continuously variable speed submersible pump.

11. The temperature controlled therapy device of claim 6, wherein the reservoir includes a refrigeration device for cooling the temperature controlled fluid contained within the reservoir.

12. The temperature controlled therapy device of claim 6, wherein the reservoir includes a heating device for heating the temperature controlled fluid contained within the reservoir.

13. The temperature controlled therapy device of claim 6, wherein the defined temperature range is for a hot therapy application having a hot temperature range of between about 95° F. and about 110° F.

14. The temperature controlled therapy device of claim 6 wherein the defined temperature range is for a cold therapy application having a cold temperature range of between about 35° F. and about 55° F.

15. The temperature controlled therapy device of claim 6, wherein the pump is a continuously variable speed submersible pump disposed within the fluid reservoir having a fluid throughput rate of between about ¼ gallons/hour and about 10 gallons/hour.

16. The temperature controlled therapy device of claim 6, wherein the pump is a hand pump disposed adjacent to the conduit for manually pumping the temperature controlled fluid through the fluid circuit.

17. The temperature controlled therapy device of claim 6, wherein the pump is a continuously variable speed submersible pump for pumping the temperature controlled fluid through the fluid circuit and thereby regulating a set-point temperature of the watertight blanket, the continuously variable speed submersible pump controlled by a pulse width modulated signal having a pulse width, wherein the pulse width of the pulse width modulated signal is varied by a pulse width modulator based on a temperature of a hot junction of a thermocouple, the temperature of the hot junction of the thermocouple determined by subtracting a sensed differential temperature provided by the thermocouple from a thermistor sensed temperature adjacently located to a cold junction of the thermocouple.

18. The temperature controlled therapy device of claim 6, further comprising a reservoir fluid indicator means adjacently located to an outer surface of the fluid reservoir and electrically connected to a reservoir sensor for alerting an operator to a fluid condition within the fluid reservoir.

19. The temperature controlled therapy device of claim 6, wherein the pump is a continuously variable speed submersible pump located within the fluid reservoir for pumping fluid from the fluid reservoir to the internal space of the watertight blanket and back to the fluid reservoir via the fluid circuit based on the control signal provided by the control circuit, thereby maintaining a temperature in the watertight blanket.

20. The device of claim 6 further comprising:

a second differential temperature sensor disposed in the reservoir for producing a second sensor signal corresponding to the temperature of the fluid in the reservoir; and the control circuit receiving the second sensor signal and in response in part to the second sensor signal, controlling the operation of the pump to substantially cease operation when the temperature of the fluid in the reservoir is outside a predetermined range of temperatures.

21. The device of claim 20 wherein the differential sensor comprises a thermocouple sensor having one thermocouple junction located in the reservoir and a second thermocouple junction located proximate the absolute temperature sensor.

* * * * *